US012708441B2

(12) United States Patent
Margheri et al.

(10) Patent No.: US 12,708,441 B2
(45) Date of Patent: Aug. 18, 2026

(54) LASER DEVICE, HAND-PIECE AND METHOD FOR LIPOLYSIS

(71) Applicant: EL.EN. S.P.A., Calenzano (IT)

(72) Inventors: Fabrizio Margheri, Calenzano (IT); Marco Tagliaferri, Calenzano (IT); Maurizio Scortecci, Calenzano (IT); Paolo Corsini, Calenzano (IT)

(73) Assignee: EL.EN. S.P.A., Calenzano (IT)

( * ) Notice: Subject to any disclaimer, the term of this patent is extended or adjusted under 35 U.S.C. 154(b) by 866 days.

(21) Appl. No.: 17/958,762

(22) Filed: Oct. 3, 2022

(65) Prior Publication Data

US 2023/0414283 A1 Dec. 28, 2023

(30) Foreign Application Priority Data

Jun. 23, 2022 (IT) ........................ 102022000013342

(51) Int. Cl.

| | |
|---|---|
| ***A61B 18/20*** | (2006.01) |
| ***A61B 18/22*** | (2006.01) |
| ***A61N 5/067*** | (2006.01) |
| *A61B 17/00* | (2006.01) |
| *A61B 18/00* | (2006.01) |
| *A61B 18/26* | (2006.01) |

(52) U.S. Cl.

CPC ............ *A61B 18/22* (2013.01); *A61B 18/201* (2013.01); *A61B 18/203* (2013.01); *A61N 5/067* (2021.08); *A61B 2017/00061* (2013.01); *A61B 2018/00464* (2013.01); *A61B 2018/263* (2013.01)

(58) Field of Classification Search

CPC ...................................................... A61B 18/20

See application file for complete search history.

(56) References Cited

U.S. PATENT DOCUMENTS

| | | | | |
|---|---|---|---|---|
| 7,975,702 | B2 | 7/2011 | Cho et al. | |
| 2012/0022510 | A1 | 1/2012 | Welches et al. | |
| 2020/0015876 | A1 * | 1/2020 | Chou | A61B 18/00 |

* cited by examiner

*Primary Examiner* — Lynsey C Eiseman

(74) *Attorney, Agent, or Firm* — McGlew and Tuttle, P.C.

(57) ABSTRACT

A device for laser lipolysis is described, comprising a treatment laser source adapted to emit radiation within a wavelength range strongly absorbed by the human body adipocytes. The device further comprises a hand-piece having a handle and a cannula that is adapted to be inserted into an adipose tissue of a patient undergoing a lipolysis treatment. An optical fiber is adapted to connect the laser source to the hand-piece, and the cannula is adapted to receive a distal portion of the optical fiber. The device further comprises a detection system, for detecting the movement speed of the hand-piece when in use, and a control unit, functionally connected to the treatment laser source and adapted to control at least one emission parameter of the treatment laser source, so as to modulate the power emitted by the treatment laser source based on the movement speed of the hand-piece detected by the detection system. The device also comprises a signaling system adapted to signal to an operator a condition of anomalous movement speed.

23 Claims, 4 Drawing Sheets

7
9
11
15
13
17
51
40
33
5
31
35
3
39
37
38
36
4
41
1

D
A

IV
IV
3
31
301
302
303
305
305A
307
310
311
312
313
315
317
319
321
324
331
332
333
335
4
41

VI
3
301
302
303
307
310
311
312
313
317
319
323
324
331
332
333
335
337

LASER DEVICE, HAND-PIECE AND METHOD FOR LIPOLYSIS

TECHNICAL FIELD

The present disclosure relates to improvements to medical equipment. Embodiments disclosed herein relate in particular to equipment and devices adapted to remove adipose layers by applying energy from laser sources.

BACKGROUND

Eating too many calories, and consuming too few calories because of not getting enough physical activity, are considered the main causes for the accumulation of adipose layers in the human body, especially in the abdominal area and in the lower part of the body. Accumulating adipose layers results in unwanted changes of the physical appearance.

In recent years, non-invasive or minimally invasive systems and methods have been developed to remove fat from the body and to reduce blemishes resulting from the accumulation of fat cells. These types of surgeries and the related equipment play an important role in modern aesthetic medicine.

Reducing the deposits of fat cells is not only an aesthetic need, but also a health need, because excess body fat and excess weight rise the risk to health, leading for example to heart diseases and type-2 diabetes, and are also related to some types of cancer, in particular colorectal and breast cancer.

The so-called body contouring is a modification of the physical appearance obtained by changing the body size and/or shape. Reducing body fat is therefore a key factor in body contouring. At the beginning, fat removal was performed through liposuction, a surgical procedure providing for injecting, into the adipose layers, chemical substances that caused the fat cell lysis, and removing fat by sucking the liquid substance resulting from the rupture of the cell membranes. Liposuction was an intervention requiring anesthesia, and not devoid of risks due to the patient's possible intolerance to the chemicals used.

Methods and equipment have been therefore investigated as an alternative to liposuction.

Nowadays, more effective and safer many methods are available for removing the fat layers, such as cryo-lipolysis and laser lipolysis, as well as electromagnetic, radiofrequency and ultrasounds lipolysis.

Laser lipolysis is particularly worth of interest. It is an effective and safe method for patients who require a modest and low-invasive body contouring treatment.

The mechanism of action of laser lipolysis is based on selective photo-hyperthermia, i.e. on selective heating the fat cells by conveying laser radiation into the adipose layers to be removed. The laser radiation, emitted by a laser source with wavelength and emission parameters suitable for the specific purpose, is conveyed into the adipose layers by means of an optical fiber, a tip of which is provided near the point of a cannula. The cannula is inserted into the tissues to be treated through a needle-cannula. The laser radiation emitted by the fiber tip is absorbed, in the form of heat, by the adipocytes, which dilate until to cause the lysis of the fat cells due to the rupture of the cellular membrane.

In addition to causing the lysis of the adipocytes, the laser radiation also stimulates the fibrous septa of connective tissue, which promotes the production of collagen and helps to reduce the orange peel skin typical of cellulite, improving the skin appearance.

Furthermore, the laser radiation helps to coagulate the small blood vessels surrounding the treated area, eliminating or reducing bleeding and swelling in the treated areas.

For all these reasons, the laser lipolysis is increasingly used in cosmetic surgery.

However, laser lipolysis is not devoid of problems. In fact, the laser radiation must be correctly dosed and uniformly distributed effectively to remove the adipose tissue without the risk of burn injuries to the patient.

U.S. Pat. No. 7,975,702 discloses a device for laser lipolysis, wherein an optical fiber conveys, to the area to be treated, not only the high-power laser radiation used for lipolysis, but also a light radiation emitted by an aiming laser source, which is visible through the patient's skin. The transcutaneous illumination by the aiming laser allows the continuous vision of the position of the fiber tip, and therefore of the treatment area.

Another important aspect is to perform the treatment uniformly and homogeneously, involving the entire volume from which the fat layer shall be removed, applying the required amount of energy to each point of the volume to be treated.

To this end, systems have been investigated for controlling the supplied energy by detecting the speed of the hand-piece that carries the cannula through which the laser energy is delivered. Some control methods are disclosed in US2012/0022510.

Despite the continuous evolution of these body contouring systems, this treatment still has many difficulties and problems for the doctor who performs it, for example in controlling the movements of the hand-piece carrying the cannula and the fiber tip inserted therein, and in correctly and optimally exploiting the laser power generated by the laser source.

As specifically known, the power emitted by the laser is usually controlled based on the movement speed of the hand-piece; but the doctor does not have adequate tools efficiently to check the correct movement of the cannula inside the patient's body.

Supplying too much energy, or supplying the right amount of energy in a too short time interval, can cause temperature to increase suddenly and excessively, with negative consequences for the patient, such as necrosis of adipose tissues and skin, seroma, loss of hair, scar formation, etc.

On the other hand, since the mechanism of action is based on selective photo-hyperthermia, if the laser energy is not efficiently delivered to the adipocytes it is impossible to achieve adequate heat accumulation and the rupture of the cellular membrane.

It is therefore fundamental to correlate the power density delivered by the laser source with the movement speed of the optical fiber conveying the radiation. In fact, too slow movements lead to a rapid accumulation of energy in a limited volume, while too fast movements do not allow the fiber to remain for the necessary time in the volume to lipolyze, with the risk of not achieving cell lysis.

It is therefore fundamental to have available a system suitable to increase the laser power, or to keep it at high values, when the hand-piece movements are fast, and to decrease the laser power when the hand-piece movements are slow.

Each laser source has a maximum emission limit; therefore, there is also a maximum limit for the movement speed of the hand-piece, above which the treatment is ineffective because the dose of energy delivered in the volume unit of the treated tissue is insufficient.

On the other hand, a slow movement of the hand-piece, forcing a decrease in the emitted power, leads to inadequate exploitation of the equipment and, ultimately, to longer treatment times, and therefore to higher intervention costs, as well as to discomfort for the patient, who must undergo more prolonged sedation.

Therefore, it would be advisable to have available a device adapted to facilitate the laser lipolysis treatment by reducing treatment times and efficiently using the laser source, with consequent advantages in terms of comfort and costs for the patient, given the same result.

SUMMARY

According to an aspect, a device for laser lipolysis is disclosed, comprising a treatment laser source adapted to emit radiation within a wavelength range strongly absorbed by the fat cells of the human body. The device further comprises a hand-piece having a handle and a cannula that is adapted to be inserted into an adipose tissue of a patient undergoing a lipolysis treatment. An optical fiber is adapted to connect the laser source to the hand-piece, and the cannula is adapted to receive a distal portion of the optical fiber. The device further comprises a detection system, for detecting the movement speed of the hand-piece when in use, and a control unit, functionally connected to the treatment laser source and adapted to control at least one emission parameter of the treatment laser source, so as to modulate the power emitted by the treatment laser source based on the movement speed of the hand-piece detected by the detection system. The device also comprises a signaling system adapted to signal to an operator a condition of anomalous movement speed.

Thanks to the signaling system, the operator can adjust the speed at which he/she moves the hand-piece so as to optimize the exploitation of the laser source without harming the patient.

As will be clearly apparent from the description below, the anomalous speed condition can be detected directly, based on the speed measured by a suitable speed detection sensor or apparatus. However, this is not strictly necessary. In fact, the emission from the laser source is modulated based on the speed; therefore, to signal an anomalous speed condition, a signal can be used that is proportional to at least one emission parameter of the laser source, for instance the power, or a parameter correlated with the delivered power, for example the pulse repetition rate of a pulsed laser source.

In practical embodiments, the signaling system is adapted to signal to the operator when the speed of the hand-piece is below a minimum threshold. The minimum threshold may be the value below which the power emitted by the laser is reduced by such an amount as to make the laser source exploitation uneconomical, i.e. a speed below which the laser source is underused.

In this way, the operator realizes that the laser source is emitting a power amount lower than that it would be able to emit, and that the treatment speed can be increased to reduce the duration of the intervention. The operator can therefore increase the movement speed of the hand-piece, thus increasing the emitted power amount and the volume of tissue treated per time unit, therefore shortening the duration of the intervention.

In advantageous embodiments, the signaling system is also adapted to signal to the operator when the speed of the hand-piece is above a maximum threshold. The maximum threshold may be the speed at which the laser source delivers the maximum power. If the operator is moving the hand-piece at a speed above the maximum threshold, the dose of energy applied to the tissues could be insufficient to reduce the adipose layers, i.e. to achieve lipolysis. The system alerts the operator, who can consequently reduce the treatment speed, thus avoiding a too long duration of the intervention, given that an insufficient dose of delivered energy would require to treat the tissues a second time.

In advantageous embodiments, the signaling system is adapted to signal to the operator when at least one of the following conditions occurs:

- the movement speed of the hand-piece lies within the interval between a maximum allowable speed and a minimum allowable speed;
- the movement speed of the hand-piece is outside the interval between a maximum allowable speed and a minimum allowable speed.

The system for detecting the movement speed of the hand-piece can be any system adapted to detect the speed in sufficiently accurate manner. The system may be selected for instance from the group including: an accelerometer; an inertial sensor, especially comprising an accelerometer and a gyroscope; a magnetic tracking system; an optical tracking system; a camera and an image processing system.

The signaling system is advantageously configured to send to the operator a signal that can be perceived by him/her without the need to withdraw his/her gaze from the operative area of the hand-piece, so as not to interfere with the intervention.

The signaling system may comprise, for example, an acoustic signaling system and/or a visual signaling system.

The visual signaling system may be adapted, for example, to provide a visual signal on the hand-piece or the cannula.

In particularly advantageous embodiments, the visual signaling system comprises at least a first aiming light source, preferably a first aiming laser source, so configured as to inject a first light beam into the optical fiber, visible through the tissues where the cannula and the optical fiber are inserted. The first light signal is controlled based on the movement speed of the hand-piece.

In some embodiments, the visual signaling system can comprise a second aiming light source, preferably a second aiming laser source, so configured as to inject a second light beam into the optical fiber, visible through the tissues where the cannula and the optical fiber are inserted; the second light signal is controlled based on the movement speed of the hand-piece, and has a color different than that of the first light signal.

In this way, the light signal alerting the operator is visible exactly in the point where the operator is performing the treatment, and it is therefore in the center of his/her field of view. The operator can promptly recognize the optical signal indicating an anomalous speed condition, and can therefore modulate the movement speed of the hand-piece without withdrawing his/her gaze from the area where he/she is performing the treatment.

The signaling system may be connected to the speed detection system, and may be controlled by a signal of the hand-piece speed. In this case, the signal is provided to the operator directly through the speed signal. However, this arrangement is not the only one possible. In fact, if the speed signal is used to modulate the power delivered by the laser, it is possible to emit an alert signal for the operator based on anomalous speed conditions (too high or too low speed) using a signal for adjusting the power emitted by the laser or a signal for measuring the emitted power. In this case, the signal of anomalous speed conditions is indirectly correlated with the movement speed of the hand-piece and directly correlated with an emission parameter of the treatment laser source.

Further advantageous features of the device are set out in the appended claims and will be described hereunder with reference to an embodiment.

According to a further aspect, a method for lipolysis treatment is disclosed, comprising the following steps:

- inserting a cannula into the tissue to be treated, the tissue containing adipocytes, and guiding an optical fiber through the cannula up to the adipose tissue;
- emitting a laser radiation through a laser source and conveying the laser radiation through the fiber into the tissue to be treated; wherein the laser radiation is adapted to cause the lysis of the adipocytes;
- moving the optical fiber and the cannula at a treatment speed in the tissue to be treated;
- modulating at least one emission parameter of the laser source based on the treatment speed;
- signaling to the operator a condition of anomalous speed of the cannula and the fiber based on a speed signal or a signal correlated with an emission parameter of the laser source.

In some embodiments, the method provides for signaling to the operator when the speed of the hand-piece is below a minimum threshold and/or when the speed of the hand-piece is above a maximum threshold.

In general, the speed minimum threshold and maximum threshold can be identified as speed values, or as values of an emission parameter of the laser source, correlated with a minimum speed threshold and maximum speed threshold. For example, the minimum speed threshold may be identified, as a matter of fact, by a minimum value of emitted power, and the maximum speed threshold may be identified by a maximum value of emitted power, for example the maximum value of the power that the laser source is able to emit.

In some embodiments, the method provides for signaling to the operator when at least one of the following conditions occurs:

- the movement speed of the hand-piece lies within the interval between a maximum allowable speed and a minimum allowable speed;
- the movement speed of the hand-piece is outside the interval between a maximum allowable speed and a minimum allowable speed.

In advantageous embodiments, the method provides for signaling, through an optical signal, a speed value and/or a speed interval, or values of emissions parameters correlated with the speed. Typically, and advantageously, signaling is performed through an optical signal conveyed through the same fiber that conveys the treatment laser radiation. To this end, one or more light sources are provided, typically laser sources, emitting light at a suitable wavelength and/or with suitable modulation of the light signal, for example a continuous or intermittent light signal giving the operator several pieces of information on the correctness of the movement speed of the hand-piece in use.

BRIEF DESCRIPTION OF THE DRAWING

The invention will be better understood by following the description below and the attached drawing, showing a non-limiting embodiment of the invention. More specifically, in the drawing.

DESCRIPTION OF PREFERRED EMBODIMENTS

Figures 1, 2:
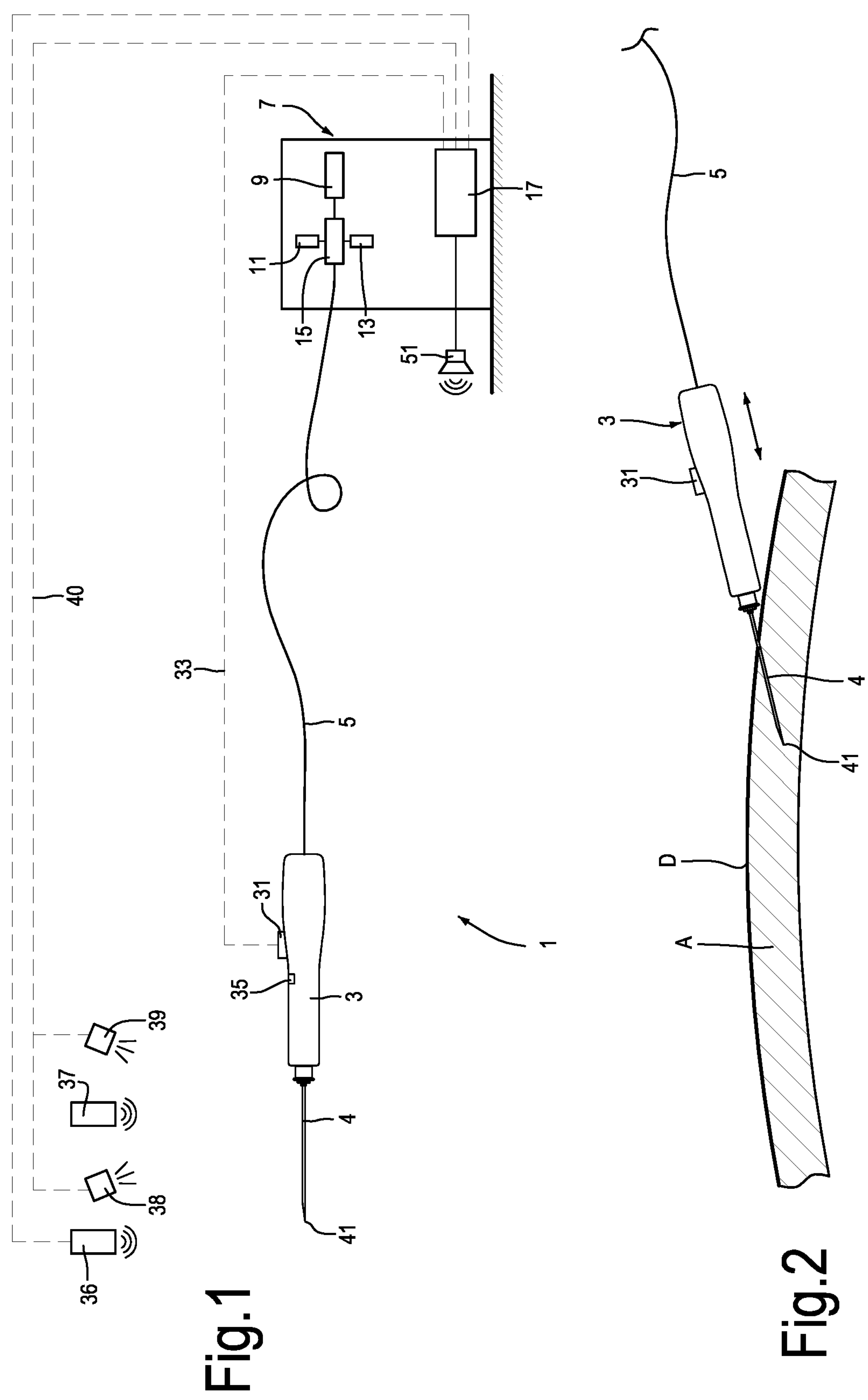
FIG. 1 shows an operation scheme of an embodiment of the device according to the invention.
FIG. 2 is a scheme illustrating the use mode of the device.
Figures 3, 4:
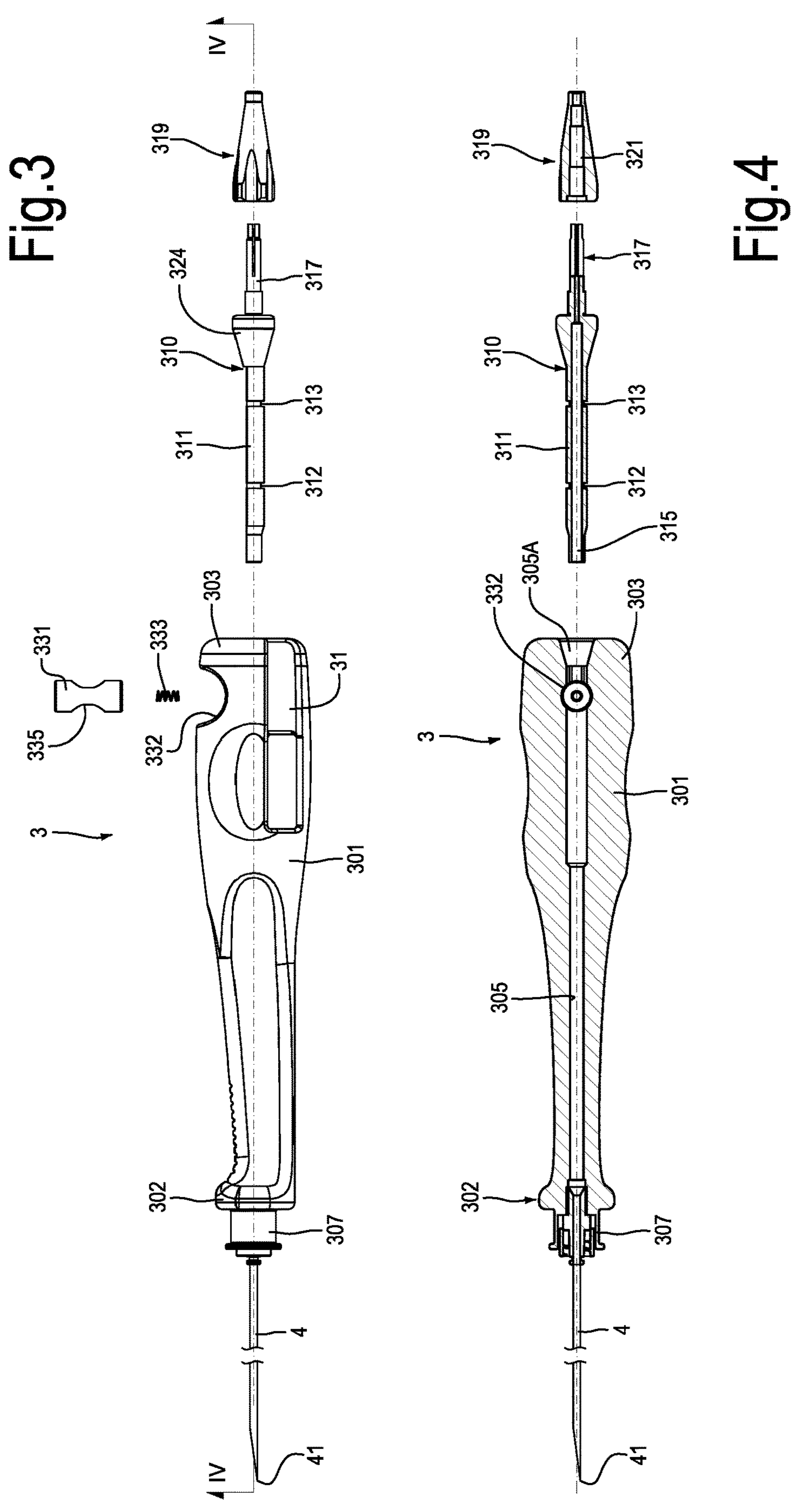
FIG. 3 is a side exploded view of a hand-piece.
FIG. 4 is a section according to IV-IV of FIG. 2.
Figures 5, 6:
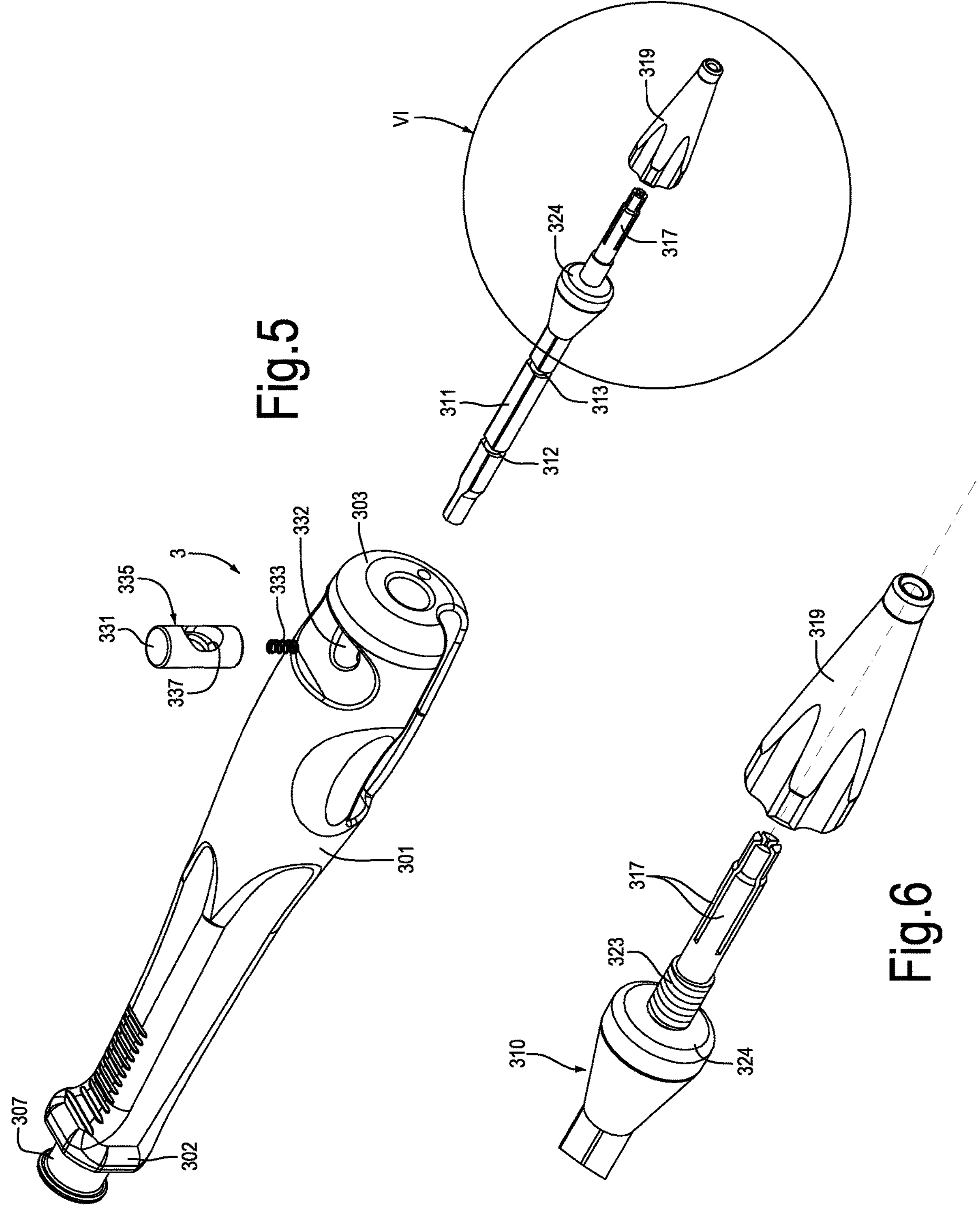
FIG. 5 shows an axonometric exploded view of the hand-piece of FIGS. 2 and 3.
FIG. 6 shows an enlargement of the detail VI from FIG. 4.

With initial reference to FIG. 1, in an embodiment, the device indicated as a whole with the reference number 1 comprises a hand-piece 3 with a cannula 4, an optical fiber 5, and an apparatus 7. The optical fiber 5 connects the hand-piece 3 to the apparatus 7, and extends with a distal end up to the distal end 41 of the cannula 4. The optical fiber 5 conveys the laser radiation from one or more laser sources of the apparatus 7 to the distal end 41 of the cannula 4.

In use, the optical fiber is positioned so that the distal end thereof protrudes, for example by 1 or 2 millimeters, from the distal end 41 of the cannula 4, as it will be explained below with reference to a use mode.

In practical embodiments, the apparatus 7 comprises a treatment laser source 9 and an aiming laser source 11. In this document, the term “treatment laser”, or “treatment laser source” refers to a laser source, the radiation whereof has the function of treating the tissues, specifically the function of lipolyzing the adipocytes; this source shall be distinguished from an aiming laser source, which has the auxiliary function of providing information to the operator, for example for identifying the position of the fiber tip under the patient skin during the treatment In further embodiments, two aiming laser sources 11, 13 can be provided, or even more than two.

To broaden the range of treatments that can be performed with the device described herein, the apparatus 7 may comprise more than one treatment laser source 9, for example two or more treatment laser sources, which emit at different frequencies and which can be selected according to the type of treatment to be performed, and therefore to the frequency (i.e. the wavelength) required for the specific treatment.

A beam combiner 15, including for example one or more dichroic mirrors (not shown), allows to inject the radiation emitted by the laser sources 9, 11, 13 into the optical fiber 5, for the purposes and in the fashion described below.

When more treatment laser sources are provided, these may be either connected to the optical fiber 5 by a laser beam combiner or selectively brought into working position.

The reference number 17 indicates a programmable control unit of the device 1. The control unit 17 is functionally connected to the laser sources 9, 11, 13 to modulate one or more emission parameters according to the criteria described below.

As well known, to perform a lipolysis treatment the operator holds the hand-piece 3 and inserts the cannula 4 inside the adipose layer A, perforating the dermis D (see FIG. 2), while the optical fiber 5 is in such a position as not to protrude from the cannula 4, to avoid damages to the fiber distal end. Once the adipose layer has been achieved, the distal end of the optical fiber 5 is extracted by a small entity, for example 1 or 2 mm, to perform the intervention. The intervention consists in irradiating laser energy from the power source 9 into the adipose layer A, thus causing a local heating which leads to the rupture of the cellular membrane of the adipocytes (i.e. the “lysis” of the adipocytes). The operator performs the treatment by moving the cannula in various directions inside the adipose layer, so as to involve the maximum possible volume of adipose layer that can be reached from a single position of access, i.e. of perforation of the skin. The movement can therefore be a movement parallel to the cannula and a movement of rotation around the cannula access hole, according to a radial pattern. This reduces the number of skin perforations required to treat the area where fat shall be removed.

One of the laser sources 11, 13 may be an aiming source, which emits a radiation that can be seen by the operator through the dermis D, so as to know in which position the fiber tip is located.

As indicated above, the laser power source 9 is a source that emits a treatment radiation, i.e. a radiation that acts on the tissues to be treated, and in particular a source that has the function of delivering power to cause the lysis of the adipocytes. However, as mentioned above, also other power sources, i.e. treatment sources, may be provided in the apparatus 7, to widen the range of treatments that can be performed with the device 1.

To perform the lipolysis, in an embodiment the treatment laser source 9 comprises a Nd:YAG laser. The treatment laser source 9 emits a preferably pulsed laser beam, with a wavelength comprised preferably between 0.75 μm and 2.5 μm, preferably between 0.9 μm and 1.44 μm, the energy per pulse being comprised between 10 mJ and 500 mJ, preferably between 50 mJ and 500 mJ.

To maximize the efficiency of the adipocytes lysis, the treatment laser source 9 has advantageously a peak power up to 3 kW, combining average power levels from 1 W to 15 W with very short pulses, for example from 50 μs to 500 μs.

In some embodiments, the pulse repetition rate of the pulsed laser is comprised between 5 Hz and 100 Hz.

The device 1 further comprises a detection system for detecting the movement of the hand-piece 3 during the treatment. This system provides information on the movement of the hand-piece which can be used by the control unit 17 to modulate one or more emission parameters.

In particular, the detection system is adapted to detect, and to provide the control unit 17 with, information on the movement speed of the hand-piece relative to the body of the patient undergoing the treatment. To this end, any direct or indirect detection system can be used for detecting the movement speed of the hand-piece. Alternative detection systems are schematically shown in the functional diagram of FIG. 1. Anyway, it should be understood that in general it is sufficient for the device 1 to comprise only a single system for detecting the movement speed of the hand-piece 1.

Just by way of example, in some embodiments the device 1 can be equipped with a detection system, schematically indicated with the reference number 31 in FIG. 1, arranged on board the hand-piece 3 and comprising an accelerometer. The system 31 is connected to the control unit 17 via a data line 33. The accelerometer measures, in a known manner, acceleration data that, when suitably integrated over time, provide information on the movement speed of the hand-piece 3 during the treatment.

In other embodiments, the detection system 31 comprises an accelerometer combined with a gyroscope system, also integrated in the hand-piece 3. The accelerometer-gyroscope system functions as an inertial sensor that can also determine the orientation and the position of the hand-piece 3.

Integrating the direct or indirect detection system for detecting the hand-piece speed inside, or on board, the hand-piece 3 is advantageous in terms of efficiency, compactness, and cost of the device, but it is not the only possible configuration.

In further embodiments, the detection system for detecting the speed of the hand-piece 3 may be provided outside the hand-piece 3 or comprise at least parts that are outside the hand-piece 3. In some embodiments, the hand-piece 3 is equipped with a magnetic field sensor 35. Outside the hand-piece 3, in a suitable position above the operating table where the patient will be positioned, external magnetic field generators can be provided, schematically shown at 36 and 37. The magnetic field sensor 35 is adapted to detect the position and the movement speed of the hand-piece 3 within the magnetic field by directly using computing resources integrated on the hand-piece 3; alternatively, the sensor may provide magnetic field signals to the control unit 17, on the basis of which the control unit 17 can determine the movement speed of the hand-piece 3.

In further embodiments, the device 1 comprises video cameras 38, 39, arranged in fixed positions above the operating table where the patient is positioned. A mark is applied to the hand-piece 3 or to the operator’s hand or arm, in a position visible to the video cameras, the mark being recognizable by a vision system to which the video cameras are connected. The images taken by the two video cameras are processed to determine the position and the speed of the mark integral with the hand-piece, and therefore to determine the movement speed of the hand-piece during the treatment. The image processing software may reside in one or both the cameras 38, 39, and the data obtained from image processing can be sent to the control unit 17 through a line 40. In other embodiments, the video data are transmitted through the line 40 to the control unit 17 that is programmed to process them for obtaining information on the movement speed of the hand-piece.

Regardless of the type of system used to determine the movement speed of the hand-piece, and therefore of the distal tip of the optical fiber 5 inside the adipose layer, the control unit 17 is adapted to modulate one or more parameters of the treatment laser source 9 in order to deliver the correct power to optimize the treatment avoiding damages to the surrounding tissues.

Typically, when the speed of the hand-piece increases, the delivered power can be increased, as this is distributed over a volume of adipose tissue which increases as the movement speed of the hand-piece increases.

In advantageous embodiments, a speed is set, below which the laser emission is interrupted, to avoid burn injuries to the patient. As the speed values gradually increase, the delivered power gradually increases until to achieve the maximum power deliverable by the laser source. When the treatment speed, i.e. the speed at which the hand-piece is moved relative to the patient, exceeds the speed at which the treatment laser delivers the maximum power, the power level remains constant.

When using a pulsed laser, power can be modulated by modulating the pulse repetition rate. By increasing or decreasing the repetition rate, the average delivered power increases or decreases.

Figure 7:
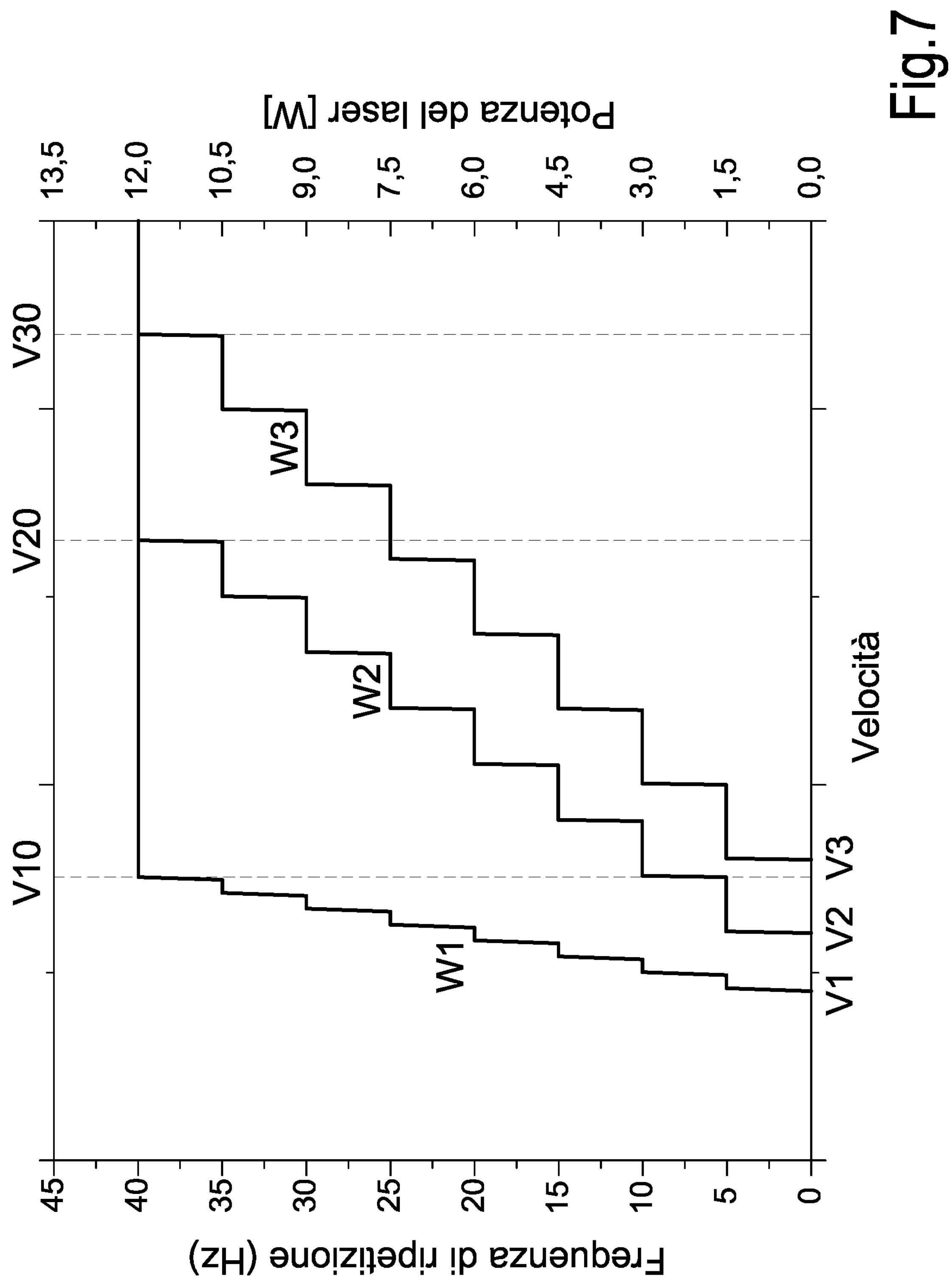
FIG. 7 shows a control diagram of the power emitted by the laser source based on a signal indicative of the speed of the hand-piece.

The power delivered by the treatment laser source 9 through the control unit 17 can be controlled in the ways shown in FIG. 7. In the diagram of FIG. 7, the signal on the abscissas is a function of the movement speed of the hand-piece, which can be obtained by the speed detection system, for example by an accelerometer on board the hand-piece 3, as described above. On the ordinates, the repetition rate in Hertz (Hz) is shown on the left, and the average power in Watts (W) is shown on the right, assuming the pulse energy is 300 mJ. The curves W1, W2, and W3 relate to three different ways of controlling the average power delivered by the treatment laser source 9.

Following the curve W1, the treatment laser source 9 is kept off when the movement speed of the hand-piece is equal to, or lower than, V1 (pulse repetition rate equal to 0 Hz). When the movement speed V1 is achieved, the pulse repetition rate is brought to 5 Hz. By increasing the movement speed, the pulse repetition rate is increased step-by-step up to a maximum of 40 Hz, which is reached when the movement speed V10 is achieved.

Following the curve W2, the treatment laser source 9 is kept off when the movement speed of the hand-piece is equal to, or lower than, V2 (pulse repetition rate equal to 0 Hz). When the movement speed V2 is achieved, the pulse repetition rate is brought to 5 Hz. By increasing the movement speed, the pulse repetition rate is increased step-by-step up to a maximum of 40 Hz, which is reached when the movement speed V20 is achieved. Similarly, following the curve W3, the emission is kept at zero, i.e. the treatment laser source is kept off, until the movement speed V3 is achieved, and it is then gradually increased until the speed V30 is achieved.

The curves W1, W2, W3 are only indicative and illustrative. The variation profiles of the emitted power can be also different than those illustrated. For example, the increase can be more gradual, with steps of 1 Hz. Essentially, in the illustrated example, the machine allows the operator to choose between three "sensitivities" of the accelerometer for controlling the delivered power, corresponding to the three exemplary curves W1, W2, W3 of the diagram of FIG. 7. In this way, the operator can decide, based on the body area to be treated, at which speed (higher or lower) the system can start emitting the maximum power. For example, the curve W1 corresponds to a "riskier" protocol, because it allows to deliver the maximum power at relatively low speed (but always with the safety that the emission stops if the movement speed is below the threshold value V1). The curve W3 corresponds to a more conservative protocol, because higher powers are delivered only with faster movements of the cannula/fiber.

Different criteria for modulating the emission from the treatment laser source 9 can also be used. For example, it is possible to keep the repetition rate constant and to modulate the average pulse power. However, controlling the delivered power based on the pulse repetition rate is currently the preferred way.

When the treatment laser source 9 is not pulsed but continuous, the control unit 17 can modulate the instantaneous power based on the speed. In some embodiments, a DC laser can be modulated to have the required power. For example, it is possible to modulate it to 100 Hz and to change modulation between 0% and 100% to have the delivered power.

From the description above it is clearly apparent that, when the treatment speed is low, the device 1 is underused. In fact, the emitted power is lower than the maximum deliverable power (12 W in the example of FIG. 7). The time required to complete the lipolysis treatment is therefore more than that required by moving the hand-piece quicker.

On the other hand, also excessively increasing the movement speed of the hand-piece involves some drawbacks, as well as the risk of damaging the underlying tissues or muscle layers. The duration of the treatment is shorter, but the result achieved could be unsatisfactory or insufficient. In fact, if the movement speed is higher than that at which the laser source 9 delivers the maximum power, the energy deposited per unit volume of treated tissue decreases and could be less than that necessary to obtain the desired effect.

According to an important aspect of the device disclosed herein, the operator is provided with a piece of information useful to verify whether he/she is operating in an optimal manner, i.e. with a movement speed of the hand-piece comprised between a minimum speed (Vmin) and a maximum speed (Vmax). The minimum speed (Vmin) can be either the speed at which the treatment laser source 9 stops delivering power or a higher speed. Similarly, the maximum speed (Vmax) can be the speed at which the treatment laser source 9 delivers the maximum power.

To this end, the device may be provided with a signaling system adapted to signal to the operator a condition of anomalous movement speed. In this description, "anomalous movement speed" means a movement speed that is not appropriate for the treatment. Typically, as mentioned above, the signaling system is adapted to signal an anomalous movement speed when the movement speed is outside an interval [Vmin, Vmax] between the minimum speed and the maximum speed defined above.

The signaling system may have various configurations. In general, it is advantageous that the signaling system provides the operator with a signal indicative of both an excessively low speed and an excessively high speed. Furthermore, it is advisable that the signaling system provides a signal that the operator can perceive without withdrawing his/her gaze from the area where he/she is performing the treatment, typically from the distal end 41 of the cannula 4, which is visible through the dermis D thanks to the light emitted by the aiming laser source.

In an embodiment, the signaling system is an acoustic system. For example, an acoustic signaling system 51 controlled by the control unit 17 can emit an acoustic signal when the movement speed is too low or too high.

In other embodiments, an optical signaling system is provided.

In some embodiments, the optical signaling system comprises one or more LEDs or other light sources arranged directly on the hand-piece 3. In some cases, the LEDs may be the same LEDs with which the accelerometer 35 is equipped. The LEDs are sufficiently close to the center of the operator's field of view to allow the operator to perceive a variation in the light signal emitted by the LEDs. LEDs of two or three different colors can be provided, for example: a first color to signal a speed lower than Vmin, a second color to signal a speed higher than Vmax, a third color, or no color, to signal a speed comprised between Vmax and Vmin.

Instead of, or in addition to, a change in the color of the optical emission, the optical signaling may be performed also by modulating the intensity or the mode of emission of the optical signal. For example: a continuous optical signal may indicate a correct movement speed (comprised between Vmax and Vmin), while a signal flashing quickly may indicate a speed higher than Vmax and a signal flashing slowly may indicate a speed lower than Vmin.

According to a currently preferred embodiment, the signaling system uses the same optical fiber 5 and one or more aiming laser sources. In this way, considerable advantages are obtained, and in particular the following: signaling is generated exactly in the point (distal end of the optical fiber 5 and of the cannula 4) where the operator's gaze must be focused; moreover, to generate this supplementary piece of information for the operator, resources (aiming laser and optical fiber) are used that are necessarily already provided on the device for other purposes, avoiding to use additional components that increase the cost of the device as well as the risk of malfunctions.

To this end, according to a particularly advantageous embodiment, if the device 1 comprises a single aiming laser source 11 or 13, the emission can be controlled based on the movement speed of the hand-piece in such a way as to emit a continuous and/or intermittent light, with variable emission modes (that is visible through the dermis D). As previously mentioned, with respect to the case where a LED on the hand-piece 3 is used, the aiming laser source 11 or 13 can emit continuous, slowly flashing or quickly flashing light depending on the movement speed of the hand-piece 3, for example: continuous light when the movement speed of the hand-piece is comprised between Vmax and Vmin; slowly flashing light when the speed is less than Vmax, quickly flashing light when the speed is less than Vmin, or vice versa.

In more efficient embodiments, two or more aiming sources 11, 13 can be used, emitting at different wavelengths and therefore generating light of different colors. These different colors, if necessary combined with a change of the emission modes (continuous, slowly flashing, quickly flashing) provide the operator with even more intuitive information on the correctness of the movement speed of the hand-piece he/she is using.

Typically, but just by way of example, an aiming laser source 11 may generate green light when the movement speed of the hand-piece is comprised between Vmax and Vmin. Conversely, an aiming laser source 13 may generate red light when the movement speed of the hand-piece is outside the range [Vmax, Vmin]. For distinguishing the two conditions of too high speed and too low speed, a continuous emission and a flashing emission can be provided respectively. Or even, the light signal of the aiming laser source can flash at high frequency when the speed of the hand-piece is above Vmax and at low frequency when the speed of the hand-piece is below Vmin, or vice versa.

Furthermore, aiming laser sources of three distinct colors may be used for the three operating conditions (correct speed, speed below Vmin, speed above Vmax).

In further embodiments, where only two aiming laser sources of different colors are used, a first source may emit green light when the speed of the hand-piece is correct (comprised between Vmax and Vmin), a second source may emit a yellow light when the speed of the hand-piece is above Vmax, and both the sources may emit at the same time, thus generating a blue signal, when the speed is below Vmin.

FIGS. 3 to 6 show in more detail an embodiment of the hand-piece 3. In this embodiment the hand-piece 3 comprises a main body 301 with a first end 302 adapted to receive the cannula 4, and an opposite second end 303, where the optical fiber 5 is inserted. The main body 301 constitutes a handle for the operator and has a through hole 305 for the passage of the optical fiber, which extends from the end 303 to the end 302. The cannula 4 is fastened in reversible manner to the main body through a coupling 307, so that it can be replaced at each intervention.

On the side opposite the cannula 4, the hand-piece comprises a guide 310 for the optical fiber. The guide 310 is adapted to be inserted in the through hole 305 of the main body 301 of the cannula to guide an optical fiber inside the main body 301 towards the first end 302.

In the illustrated embodiment, the guide 310 comprises a tubular portion 311 with two outer annular grooves 312, 313 and a through hole 315 extending along the longitudinal axis of the guide 310. The tubular portion 311 extends at the back with elastically deformable appendages 317 separated from each other by longitudinal notches. The appendages 317 extend longitudinally along the through hole 315 of the guide and define the rear end part thereof. The appendages 317 constitute fastening elements for fastening the fiber in the guide 310. The fiber is fastened by fixing a fastening cap 319 on the portion formed by the appendages 317, so that the fastening cap is arranged coaxially with the through hole 315 and to the appendages 317, tightening these latter radially against an optical fiber inserted in the through hole 315.

To this end, in the illustrated embodiment, the fastening cap 319 is provided with a female thread and can be screwed onto a threaded area 323 (FIG. 6) of the tubular portion 311 of the guide 310. The reference number 324 indicates an abutment on which the fastening cap 319 rests when it is screwed onto the threaded area 323.

The fastening cap 319 has a through hole 321 that, when the fastening cap is screwed onto the tubular portion, is coaxial with the through hole 315. In this way, the optical fiber 5 can be inserted through the fastening cap 319, the appendages 317 and the tubular portion 311. When the fastening cap 319 is screwed onto the tubular portion 311 of the guide 310, the elastic appendages 317 are pressed radially towards one another in approaching the axis of the through hole 321, due to the effect of the thrust exerted on the elastic appendages by the through hole 321, suitably shaped for this purpose. The optical fiber 5 inserted in the guide 310 is thus blocked in axial position with respect to the guide.

A blocking and releasing button or slider 331 is housed in a transverse seat 332 of the main body 301 of the hand-piece 3 and is elastically stressed in radial direction by a spring 333. The slider 331 is transversely perforated at 335. When mounted, the guide 310 is inserted through the hole 335, which is therefore coaxial with the through hole 305 of the main body 311 and the through hole 315 of the guide 310. In the through hole 335 of the slider 331 it has an inner annular projection 337 that co-acts with any of the outer grooves 313, 313, with which the tubular portion 311 of the guide 310 is provided.

All the components of the hand-piece can be suitably sterilized for surgical use.

With this arrangement, the optical fiber and the hand-piece can be used in the following way. When the guide 310 is applied to the main body 301 of the hand-piece 3 and the fastening cap 319 engages the thread 323, without being screwed on it, the operator inserts the distal end of the optical fiber 5 through the hole 321 of the fastening cap 319 until the distal end protrudes from the opposite side with respect to the elastic appendages 317, and brings the fiber tip to the end 41 of the cannula 4. Once this position has been reached, the fastening cap 319 is screwed, thus tightening the elastic appendages 317 and blocking the optical fiber between the appendages and the guide.

The fastening position of the optical fiber 5 and the length of the portion of optical fiber protruding from the guide 310 can be adjusted based on the specific needs. This allows, among other things, to reuse the optical fiber several times, even if the fiber tip is damaged and/or is deliberately cut to reuse the optical fiber in subsequent operations, without changing the entire optical fiber. The possibility of adjusting the length of the fiber protruding from the guide 310 also allows to use, with the same fiber, cannulas 4 of different lengths, based for example on the area to be treated. The cannula 4 may also be replaced with another one of a different length during the same intervention, thanks to the possibility of quickly adjusting the length of the fiber protruding from the guide 310 in the main body 301 of the hand-piece 3.

In the embodiment illustrated in FIGS. 3 to 6 a further advantageous feature is provided, consisting in the possibility of moving the optical fiber 5, fastened to the guide 310, in two distinct positions to carry out different phases of the intervention.

To this end, the following are provided: the slider 331 with the through hole 335 and the inner annular projection 337, as well as the outer annular grooves 312, 313 of the tubular portion 311 of the guide 310. The guide 310 is inserted in the hole 305 of the main body 301 of the hand-piece 3 passing through the hole 335 of the slider 331, when this latter is inserted in the seat 332, with the through hole 335 aligned with the hole 305. The guide 310 is inserted in the main body 301 of the hand-piece until the groove 313 engages the inner annular projection 337. At this point, with the fastening cap 319 at least partially unscrewed and the elastic appendages 317 moved away from each other, the operator inserts the optical fiber 5 until the tip or distal end thereof is at the point of the cannula 4. Preferably, in this step the fiber tip is so positioned relative to the cannula 4 as to be in the desired position for carrying out the intervention. Once this position has been achieved, the fastening cap 319 is screwed by tightening the elastic appendages 317 on the optical fiber 5, which in this way remains axially blocked in the guide 310.

Then, in order to insert safely the cannula 4 in the layer of adipose tissues A of the patient by perforating the dermis D, without the risk of damaging the optical fiber 5, the operator presses the slider 331, releasing the guide 310 from the annular projection 337, and slightly retracts the guide 310. The slider 331 is released and the guide 310 is further retracted until the inner annular projection 337 snaps elastically, under the thrust of the spring 333, into the annular groove 312. In this position, the tip of the fiber 5 is integrally housed inside the cannula 4 and does not protrude from it. The operator inserts the cannula 4 in the adipose layer A by penetrating the dermis D, without risk of damaging the fiber.

Then, the guide 310 is released by pressing the slider 331, and returned to the axial position where the groove 313 co-acts with the inner annular projection 337, i.e. the position where the tip of the fiber 5 is in the point 41 of the cannula 4, or close to it. When the fiber 5 is in this position, the treatment can start by actuating the treatment laser source 9 and the aiming laser source(s) and moving the hand-piece, with the cannula 4 inside the adipose layer A, at the correct speed (controlled as described above). The operator controls the position and movement of the cannula through the light radiation of the aiming laser source, which is visible through the dermis D.

In practice, the two annular grooves 312 and 313 define two mutual positions between the optical fiber 5 and the cannula 4, that are suitably: a working position, where the tip of the optical fiber 5 is close to the point 41 of the cannula 4 (when the guide 310 engages the groove 313 at the inner annular projection 317); and a retracted perforation position, where the fiber is protected inside the cannula 4, in a back position spaced from the point 41 (when the guide 310 engages the groove 312 at the annular projection 317).

The hand-piece described above can also be used in devices other than those illustrated above, whenever it is desirable to have similar functions.

What is claimed is:

1. A device for laser lipolysis; wherein the device comprises:

at least one treatment laser source adapted to emit radiation within a wavelength range strongly absorbed by human body adipocytes;

a hand-piece comprising a handle and a cannula adapted to be inserted into the adipose tissue of a patient undergoing a lipolysis treatment;

an optical fiber adapted to connect the treatment laser source to the hand-piece, the cannula being adapted to receive a distal portion of the optical fiber;

a detection system for detecting the movement speed of the hand-piece when in use;

a control unit, functionally coupled to the treatment laser source and adapted to control at least one emission parameter of the treatment laser source, configured to modulate the power emitted by the treatment laser source based on the movement speed of the hand-piece detected by the detection system;

a visual signaling system adapted to signal an anomalous speed condition to an operator, wherein the visual signaling system comprises at least one first aiming light source adapted to inject a first light beam into the optical fiber, the first light beam being visible through tissues in which the cannula and the optical fiber are inserted, wherein the control unit is configured to control the first aiming light source based on the detected movement speed of the hand-piece to provide an operator with information on the movement speed of the hand-piece.

2. The device of claim 1, wherein the signaling system is adapted to signal to the operator when the speed of the hand-piece is below a minimum threshold.

3. The device of claim 1, wherein the signaling system is adapted to signal to the operator when the speed of the hand-piece is above a maximum threshold.

4. The device of claim 1, wherein the signaling system is adapted to signal to the operator when at least one of the following conditions occurs:

the movement speed of the hand-piece lies within the interval between a maximum allowable speed and a minimum allowable speed;

the movement speed of the hand-piece is outside the interval between a maximum allowable speed and a minimum allowable speed.

5. The device of claim 1, wherein the signaling system is adapted to signal to the operator when the speed of the hand-piece is such that the power emitted by the treatment laser source is below a threshold value.

6. The device of claim 1, wherein the signaling system is adapted to signal to the operator when the speed of the hand-piece is above a value at which the treatment laser source emits a preset maximum power.

7. The device of claim 1, wherein the system for detecting the movement speed of the hand-piece is selected from the group consisting of: an accelerometer; an inertial sensor; a magnetic tracking system; an optical tracking system; a camera and an image processing system; a combination thereof.

8. The device of claim 1, wherein the first aiming light source is a laser source.

9. The device of claim 8, wherein at least one of the light sources comprises a laser diode.

10. The device of claim 1, wherein the visual signaling system comprises a second aiming light source, adapted to inject a second light beam into the optical fiber, visible through the tissues where the cannula and the optical fiber are inserted; and wherein the second light signal is controlled by the control unit based on the movement speed of the hand-piece, and has a color different than that of the first light signal.

11. The device of claim 1, wherein the signaling system comprises an acoustic signaling system.

12. The device of claim 1, wherein the signaling system is connected to the speed detection system and is controlled by the control unit through a signal of the hand-piece speed.

13. The device of claim 1, wherein the signaling system is connected to the control unit and is controlled by the control unit through at least one of the following: a signal of the hand-piece speed; a laser source emission adjusting signal.

14. The device of claim 1, wherein the control unit is adapted to reduce the emitted power if the speed of the hand-piece is below a first minimum threshold.

15. The device of claim 1, wherein the treatment laser source is a pulsed laser source, and wherein the control unit is adapted to modulate the pulse repetition rate based on the movement speed of the hand-piece.

16. The device of claim 15, wherein the pulse duration of the laser source is comprised between 50 microseconds and 500 microseconds.

17. The device of claim 15, wherein the energy per pulse of the treatment laser source is comprised between 10 mJ and 500 mJ.

18. The device of claim 15, wherein the peak power per pulse of the treatment laser source is comprised between 0,1 kW and 3 kW.

19. The device of claim 15, wherein the pulse repetition rate of the treatment laser source is comprised between 1 Hz and 200 Hz, or between 4 Hz and 100 Hz.

20. The device of claim 14, wherein the treatment laser source is a continuous laser source and wherein the control unit modulates the fluence of the treatment laser source based on the movement speed of the hand-piece.

21. The device of claim 1, wherein the wavelength of the treatment laser source is within the near-infrared region, or comprised between 0.75 micrometers and 2.2 micrometers, or comprised between 0.98 micrometers and 1.45 micrometers, or comprised between 1.2 micrometers and 1.45 micrometers.

22. The device of claim 15, wherein the energy per pulse of the treatment laser source is comprised between 50 mJ and 500 mJ.

23. The device of claim 1, wherein the system for detecting the movement speed of the hand-piece is selected from the group consisting of: an accelerometer; an inertial sensor comprising an accelerometer and a gyroscope; a magnetic tracking system; an optical tracking system; a camera and an image processing system; a combination thereof.

* * * * *